(12) United States Patent
Fallon et al.

(10) Patent No.: US 8,833,374 B2
(45) Date of Patent: Sep. 16, 2014

(54) INTRA-ORAL MANDIBULAR ADVANCEMENT APPLIANCE

(75) Inventors: James C. Fallon, Laguna Niguel, CA (US); Richard Jung, Laguna Niguel, CA (US); James S. Fallon, Laguna Niguel, CA (US)

(73) Assignee: James S. Fallon, Laguna Niguel, CA (US)

( * ) Notice: Subject to any disclaimer, the term of this patent is extended or adjusted under 35 U.S.C. 154(b) by 390 days.

(21) Appl. No.: 13/199,383

(22) Filed: Aug. 29, 2011

(65) Prior Publication Data

US 2012/0145166 A1    Jun. 14, 2012

Related U.S. Application Data

(60) Provisional application No. 61/457,027, filed on Dec. 13, 2010.

(51) Int. Cl.
  *A61F 5/56* (2006.01)
  *A61C 7/08* (2006.01)
(52) U.S. Cl.
  CPC ..................... *A61F 5/566* (2013.01)
  USPC ............... 128/848; 128/859; 128/861; 433/6; 433/68; 433/69
(58) Field of Classification Search
  CPC ..................... A61F 5/56; A61C 7/08
  USPC .................. 128/848, 859, 861–862; 602/902; 433/6–7, 68–69
  See application file for complete search history.

(56) References Cited

U.S. PATENT DOCUMENTS

| | | | | |
|---|---|---|---|---|
| 5,044,950 | A | * | 9/1991 | Hobish et al. ................. 433/69 |
| 5,692,493 | A | * | 12/1997 | Weinstein et al. ....... 128/200.23 |
| 5,876,199 | A | * | 3/1999 | Bergersen ........................ 433/6 |
| 6,161,542 | A | | 12/2000 | Halstrom |
| 8,205,617 | B2 | * | 6/2012 | Scarberry et al. ............. 128/848 |
| 2007/0209666 | A1 | | 9/2007 | Halstrom |
| 2009/0241969 | A1 | | 10/2009 | Walker |
| 2010/0261133 | A1 | | 10/2010 | Lax |
| 2011/0017220 | A1 | * | 1/2011 | Lindsay et al. ............... 128/848 |
| 2011/0099846 | A1 | | 5/2011 | Fischer |

* cited by examiner

*Primary Examiner* — Patricia Bianco
*Assistant Examiner* — Camtu Nguyen
(74) *Attorney, Agent, or Firm* — Morland C. Fischer

(57) ABSTRACT

An intra-oral mandibular advancement appliance to be inserted in the mouth of a patient so as to maintain an open airway to the patient's throat and thereby improve breathing during sleep. The mandibular advancement appliance has particular application for use by those wishing to reduce the effects of snoring and/or sleep apnea. The appliance includes an upper tray assembly against which is seated the patient's teeth carried by his upper jaw and a lower tray assembly against which the patient's teeth carried by his lower jaw are seated. The lower tray assembly is mated to and slidably adjustable by the patient relative to the upper tray assembly. By virtue of the foregoing, the position of the patient's lower jaw can be selectively and continuously moved forward with respect to the position of the upper jaw to prevent an occlusion of the airway as the patient's condition changes over time.

20 Claims, 7 Drawing Sheets

INTRA-ORAL MANDIBULAR ADVANCEMENT APPLIANCE

CROSS-REFERENCES TO RELATED APPLICATIONS

This application is related to Provisional Patent Application No. 61/457,027 filed Dec. 13, 2010.

BACKGROUND OF THE INVENTION

1. Field of the Invention

This invention relates to an intra-oral mandibular advancement appliance to be inserted in the mouth of a patient so that the position of the patient's lower jaw can be continuously adjusted relative to the upper jaw so as to improve the patient's breathing during sleep and thereby reduce the effects of snoring and/or sleep apnea. The aforementioned adjustment can be easily and selectively accomplished by the patient over time without the use of special tools, springs, having to remove and install fasteners, or requiring the assistance of healthcare personnel.

2. Background Art

Snoring and sleep apnea are typically caused by obstructions (i.e., occlusions) to a patient's airway to his throat through which the patient breathes during sleep. By way of example, as a consequence of age, being overweight, medical and physical conditions, and the like, the palate and soft tissue around the patient's throat are known to relax and collapse and thereby cut off or restrict the flow of air to the patient's throat while he is asleep. Sometimes, the patient's tongue can fall backwards towards his throat so as to also adversely affect breathing. The prolonged cut off of an air supply can cause the patient to choke, lose valuable sleep and, in some extreme cases, suffer heart impairment.

One means that has proven successful in treating snoring and sleep apnea is a CPAP machine. In this case, air under pressure is continuously blown down the patient's throat to maintain an open airway. However, using a CPAP machine also requires the use of a mask that is strapped over the patient's nose and/or mouth. Wearing such a mask is uncomfortable to many patients. Patients who are CPAP intolerant will be unable to receive the benefits available therefrom.

To avoid the use of the mask common to CPAP machines and, as an alternative means for treating snoring and sleep apnea, oral appliances have been proposed to be inserted in the patient's mouth and used while sleeping. Such devices enable the patient's upper and lower jaws to be positioned relative to one another as needed to maintain an open breathing passage. Following a trial period, the settings in some conventional oral appliances are fixed and locked. However, no future adjustments can be made to account for patient discomfort and ineffectiveness of the device. Therefore, these appliances can prove to be ineffectual over time as a consequence of their being unable to respond to the changing conditions of the patient.

In certain other conventional oral appliances, adjustments are possible after the original settings have been made. The adjustments in this case often require the use of special tools, springs, the often complicated removal and installation of fasteners, and the assistance of healthcare workers. Hence, the patient may be unable to quickly or easily make the needed adjustments by himself. What is more, such adjustments are frequently course in nature (e.g., low, medium and high) which inhibits making fine adjustments to the position of the patient's upper or lower jaw as might be required to satisfy the specific needs of the patient on a continuous basis.

SUMMARY OF THE INVENTION

Briefly, and in general terms, an intra-oral mandibular advancement appliance is disclosed which is adapted to be inserted in the mouth of a patient so as to maintain an open airway to the patient's throat in order to improve breathing during sleep. The mandibular advancement appliance herein disclosed has particular application for use by those who suffer from snoring and/or sleep apnea. The appliance includes an arcuate upper tray assembly to be engaged by the teeth carried by the patient's upper jaw and an arcuate lower tray assembly to be engaged by the teeth of the patient's lower jaw. The lower tray assembly is mated to and slidably adjustable relative to the upper tray assembly so as to cause the lower jaw of the patient to move forward of the upper jaw. The slidable adjustment of the lower tray assembly relative to the upper tray assembly can be selectively and continuously performed by the patient so that his lower jaw can be advanced in small increments as is required to meet the patient's changing needs over time. The foregoing adjustment can be made by the patient without the use of special tools, springs, having to remove and install fasteners, or the assistance of healthcare personnel.

The upper tray assembly of the mandibular advancement appliance includes a relatively soft upper bite impression tray which is attached to a relatively hard upper chassis. The lower tray assembly includes a relatively soft lower bite impression tray which is attached to a relatively hard lower chassis. Each of the upper and lower bite impression trays has a bite channel within which an impression of the teeth of the patient is made when the upper and lower tray assemblies are first heated and the patient then bites down on and compresses the soft bite impression trays against the hard chassis.

A pair of position adjustment blocks standing upwardly from opposite sides of the arcuate lower tray assembly are slidably received by respective locking channels formed in opposite sides of the arcuate upper tray assembly, whereby the upper and lower tray assemblies are mated together one above the other. The position adjustment blocks and the locking channels have sets of teeth running therealong which mesh together to lock the position of the lower tray assembly below the upper tray assembly. When it is desirable to change the position of the lower tray assembly to cause a corresponding change (i.e., advancement) of the patient's lower jaw, compressive squeezing forces are applied by the patient to position control push pads located at opposite sides of the arcuate lower tray assembly. The compressive forces temporarily change the shape of the lower tray assembly so that the teeth along the position control blocks move out of their locking engagement with the teeth along the locking channels. The position of the lower tray assembly is slidably adjusted by pushing the position control blocks of the lower tray assembly through the locking channels of the upper tray assembly.

The mandibular advancement appliance also has a tongue rest that is attached to one end of a flexible tongue support wire. The opposite end of the tongue support wire is detachably connected to the lower tray assembly so that the tongue rest can be removed depending upon the needs and comfort of the patient. With the tongue support wire connected, the tongue rest lays on the patient's tongue to prevent the tongue from flapping backwards and possibly occluding the patient's airway.

DESCRIPTION OF THE PREFERRED EMBODIMENT

Figure 1:
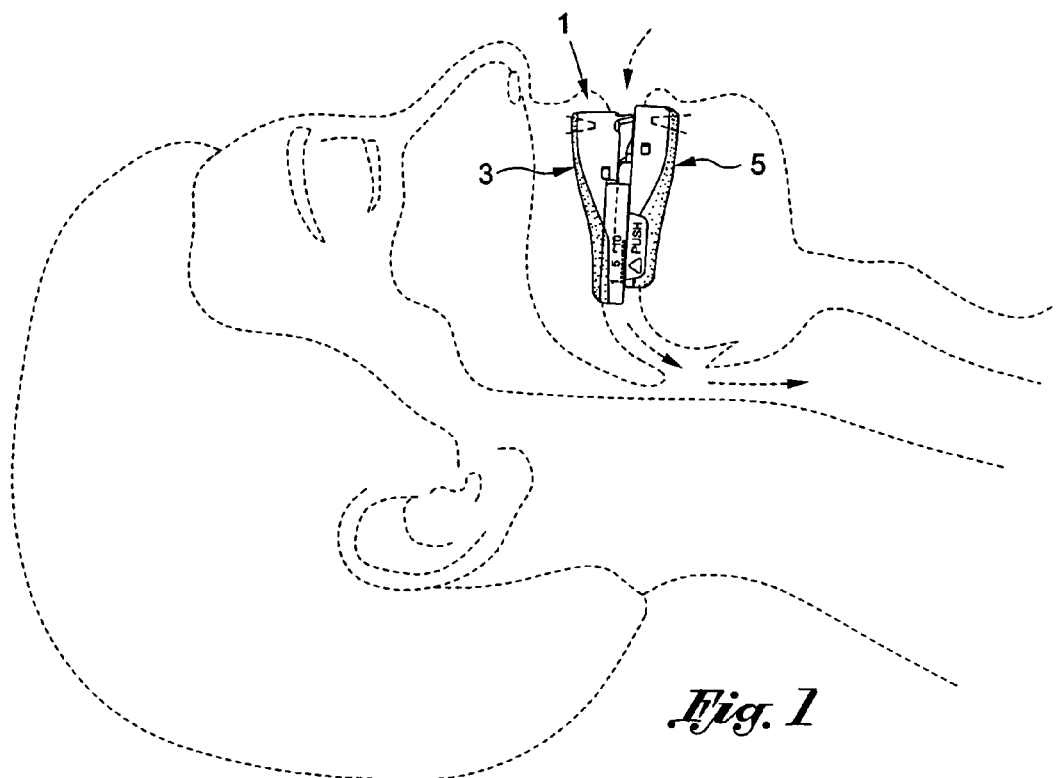
FIG. 1 shows the intra-oral mandibular advancement appliance of this invention inserted in the mouth of a sleeping patient.

Referring to the drawings, details are now provided of the intra-oral mandibular advancement appliance 1 according to a preferred embodiment of the present invention. As will be described, the mandibular advancement appliance 1 is adapted to fit within the mouth of a patient so that his lower jaw can be advanced forward relative to the upper jaw by a variable distance that can be selectively and continuously controlled by the patient. By virtue of the foregoing, the appliance 1 can be manually adjusted by the patient without the use of tools, springs, the removal and insertion of fasteners, or the intervention by medical personnel so that an airway to the throat will remain open whereby to promote adequate breathing while the patient sleeps. It may therefore be appreciated that the intra-oral mandibular advancement appliance 1 has particular application for use by a patient wishing to cope with snoring and/or sleep apnea.

Referring initially to FIGS. 7-10 of the drawings, the appliance 1 includes an upper tray assembly 3 and a lower tray assembly 5. As will be described in greater detail hereinafter when referring to FIGS. 3-6, the upper and lower tray assemblies 3 and 5 are mated together so as to lie one above the other such that the lower tray assembly 5 can be advanced forwardly by the patient relative to upper tray assembly 3. A forward advancement of the lower tray assembly 5 causes a correspondingly forward displacement of the patient's lower jaw relative to his upper jaw to enable the size of the airway to the patient's throat to be regulated in order to avoid an occlusion and thereby relieve the effects of snoring and/or sleep apnea.

The upper tray assembly 3 of the intra-oral mandibular advancement appliance 1 includes an upper bite impression tray 7 and an upper chassis 9 to be press fit together so that the tray 7 lies above the chassis 9. Both the upper bite impression tray 7 and lower chassis 9 have a generally arcuate configuration to match the bite pattern of the teeth carried by the upper jaw. The upper bite impression tray 7 is manufactured from a relatively soft and impressionable material such as, for example, that known commercially as EVA manufactured by Dupont. The lower chassis 9 is manufactured from a relatively hard and rigid material such as, for example, polycarbonate.

The lower tray assembly 5 of the intra-oral mandibular advancement appliance 1 includes a lower chassis 10 and a lower bite impression tray 12 to be press fit together so that the chassis 10 lies above the tray 12. Like the upper tray 7 and the upper chassis 9 of the upper tray assembly 3, the lower chassis 10 and the lower bite impression tray 12 of the lower tray assembly 5 each have a generally arcuate configuration to match the bite pattern of the teeth carried by the lower jaw. Also like the upper tray 7 and the upper chassis 9, the lower chassis 10 is manufactured from a relatively hard and rigid material, while the lower bite impression tray 12 is manufactured from a relatively soft and impressionable material.

A bite channel 14 (best shown in FIG. 7) runs around the top of the arcuate upper bite impression tray 7 of the upper tray assembly 3. The bite channel 14 is sized to receive therewithin the set of teeth of the patient carried by his upper jaw bone. Inasmuch as the relatively soft upper bite impression tray 7 lays over and against the relatively hard upper chassis 9, a biting force generated by the patient's upper set of teeth and applied to the upper bite impression tray 7 will shape the bite channel 14 thereof in a manner that will soon be described.

A plurality of (e.g., six) locating pins 16 (best shown in FIG. 8) project downwardly from the bottom of the upper bite impression tray 7. In addition, a plurality of (e.g., five) locating tabs 18 (also best shown in FIG. 8) project inwardly and outwardly from the arcuate upper bite impression tray 7. The pluralities of locating pins 16 and locating tabs 18 enable the upper bite impression tray 7 to be pressed into attachment with the upper chassis 9 to complete the upper tray assembly 3.

A corresponding plurality of locating pin holes 20 extend through the upper chassis 9 of the upper tray assembly 3. Likewise, a corresponding plurality of locating tab slots 22 are formed in the upper chassis 9. The locating pin holes 20 and the locating tab slots 22 of the upper chassis 9 are positioned to receive respective ones of the locating pins 16 and the locating tabs 18 of the upper bite impression tray 9 so that the upper bite impression tray 7 is seated upon and attached to the upper chassis 9 in response to a squeezing force or pressure applied thereagainst in order to complete the upper tray assembly 3 of the mandibular advancement appliance 1.

A pair of guide retention walls 26 (best shown in FIG. 8) are located at the front of the arcuate upper chassis 9. The guide retention walls 26 run in spaced parallel alignment with one another along the bottom of the upper chassis 9. A guide path 28 is established in the space between the pair of guide retention walls 26. As will soon be described, a centering guide (designated 46 in FIG. 7) which projects upwardly from the lower chassis 10 of the lower tray assembly 5 is slidably received through the guide path 28 between guide walls 26 when the upper and lower tray assemblies 3 and 5 are mated together.

Figure 7:
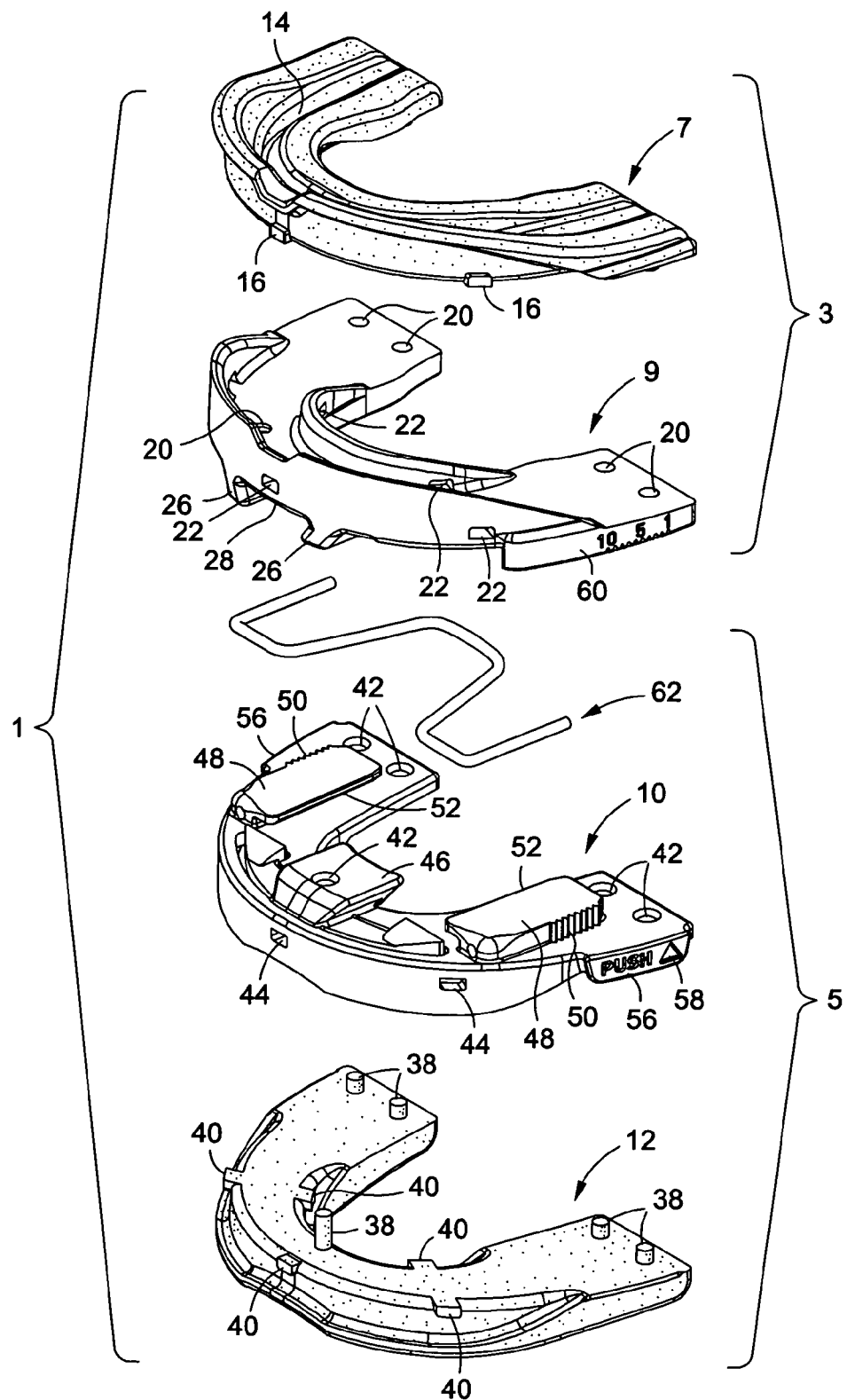
FIGS. 7 and 8 show top and bottom exploded views of the mandibular advancement device.
Figure 8:
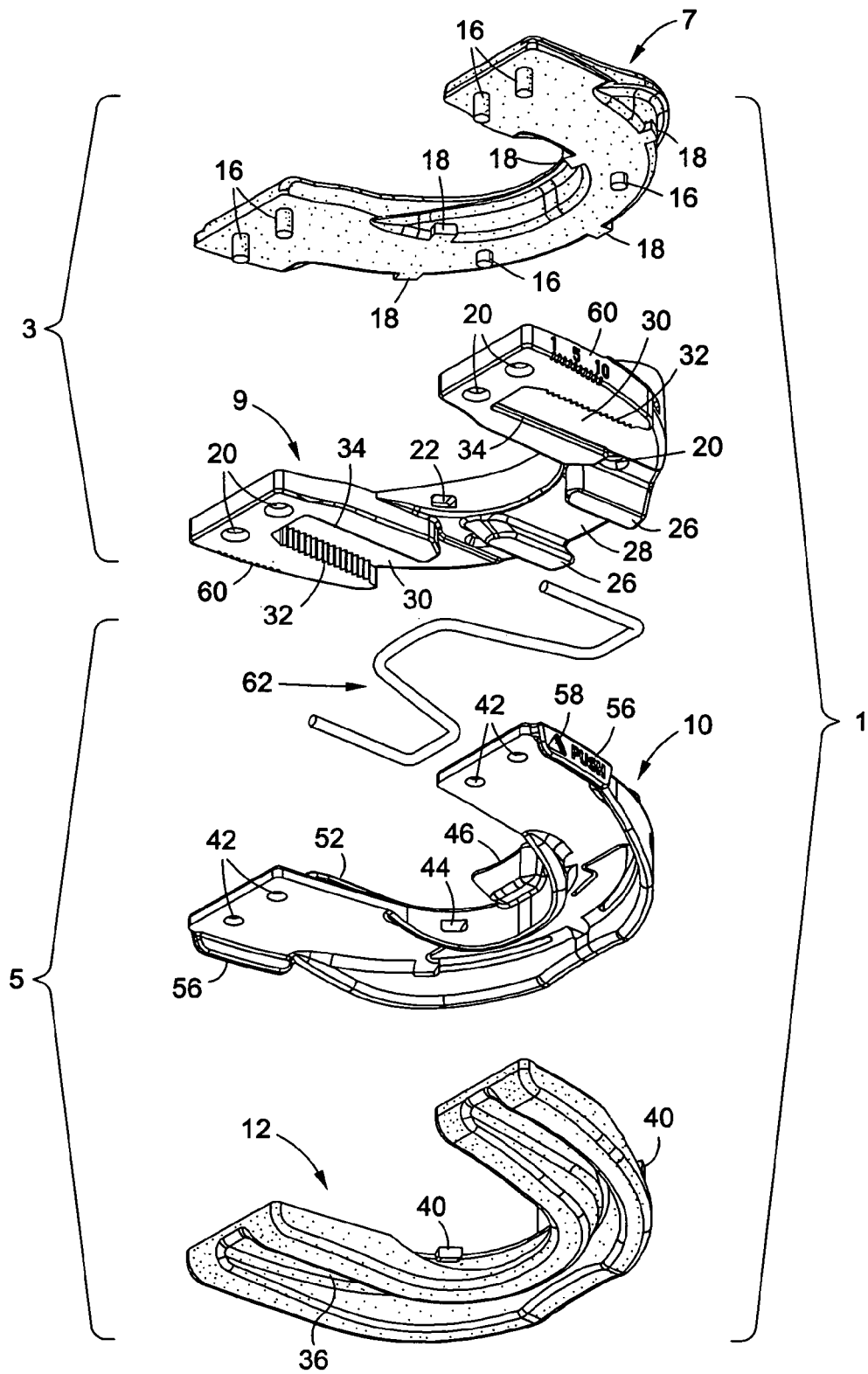

Located at each side and formed in the bottom of the upper chassis 9 behind the guide retention walls 26 is a locking channel 30 (also best shown in FIG. 8). The locking channels 30 run parallel to each other and to the guide path 28 at the front of the upper chassis 9. A row of teeth 32 is formed (e.g., molded) along one side of each locking channel 30. A catch 34 runs along and projects from the opposite side of each locking channel 30 so as to extend over and above the channel 30. As will also be described, at the same time that the centering guide 46 of the lower chassis 10 is slidably received by the guide path 28 of the upper chassis 9, a pair of position adjustment blocks (designated 48 in FIGS. 7 and 9) which stand upwardly from the lower chassis 10 are pushed through and ride into interlocking engagement with the locking channels 30 of the upper chassis 9 to retain the positions of the upper and lower tray assemblies 3 and 5 relative to one another. However, it is to be understood that either one of the upper tray assembly 3 or the lower tray assembly 5 can have the position adjustment blocks 48 standing upwardly therefrom, and the other one of the upper and lower assembly tray assemblies 3 and 5 can have the locking channels 30 formed therein.

A bite channel 36 (best shown in FIG. 8) runs around the bottom of the arcuate lower bite impression tray 12 of the lower tray assembly 5. The bite channel 36 is sized to receive therewithin the set of teeth of the patient carried by his lower jaw bone. Inasmuch as the relatively soft lower bite impression tray 12 lays below and against the relatively hard lower chassis 10, a biting force generated by the patient's lower set of teeth and applied to the lower bite impression tray 12 will shape the bite channel 36 at the same time that the bite channel 14 from the upper bite impression tray 7 is being shaped.

Projecting upwardly from the lower bite impression tray 12 of the lower tray assembly 5 are a plurality of (e.g., five) locating pins 38 (best shown in FIG. 7). A plurality of (e.g., five) locating tabs 40 (also best shown in FIG. 7) project inwardly and outwardly from the arcuate lower bite impression tray 12. The pluralities of locating pins 38 and locating tabs 42 enable the lower bite impression tray 12 to be pressed into attachment with the lower chassis 10 to complete the lower tray assembly 5.

Corresponding pluralities of locating pin holes 42 and locating tab slots 44 are formed in the lower chassis 10 of the lower tray assembly 5. The locating pin holes 42 and the locating tab slots 44 of the lower chassis are positioned to receive respective ones of the locating pins 38 and the locating tabs 40 of the lower bite impression tray 12 so that the lower chassis 10 is seated upon and attached to the lower bite impression tray 12 in response to a squeezing force or pressure applied thereagainst in order to complete the lower tray assembly 5 of the mandibular advancement appliance 1.

A centering guide 46 (best shown in FIG. 7) to which reference was made earlier is located at the front of the arcuate lower chassis 10. The centering guide 46 stands upwardly from the top of the lower chassis 10 between the aforementioned pair of position adjustment blocks 48. One of the locating pin holes 42 of the lower chassis 10 runs through the centering guide 46 for the receipt therewithin of an opposing one of the locating pins 38 at the front of the lower bite impression tray 12. As previously described, the centering guide 46 of the lower chassis 10 is slidably received through the guide path 28 of the upper chassis 9 when the upper tray assembly 3 is mated to the lower tray assembly 5 to complete the mandibular advancement appliance 1.

Located at opposite sides of and standing upwardly from the upper chassis 10 behind the centering guide 46 is the pair of position adjustment blocks 48 (also best shown in FIG. 7). A row of teeth 50 is formed (e.g., molded) along one side of each position adjustment block 48. A lip 52 runs along and projects from the opposite side of each of the position adjustment blocks 48, such that the lips 52 are disposed in spaced opposing alignment.

As was also previously described, at the same time that the centering guide 46 of the lower chassis 10 is slidably received by the guide path 28 of the upper chassis 9, the pair of position adjustment blocks 48 of the lower chassis 10 are correspondingly aligned to be slidably received by and ride through respective ones of the locking channels 30 of the upper chassis 9. Likewise, the opposing lips 52 projecting from the position adjustment blocks 48 slide below and are captured by the catches 34 which project over and above the locking channels 30 (see FIG. 5), whereby the upper and lower tray assemblies 3 and 5 are mated together so as to be held in place one above the other (best shown in FIGS. 3 and 4). In this same regard, the teeth 50 along the pair of position adjustment blocks 48 will move into releasable locking engagement with and mesh against the teeth 32 along the locking channels 30. However, any suitable interlocking ratchet means may be substituted for the opposing sets of meshing teeth 32 and 50.

As an important feature of this invention, the patient is provided with the ability to release the locking engagement of the teeth 50 of the position adjustment blocks 48 with the teeth 32 of the locking channels 30. By virtue of the foregoing, the position of the lower tray assembly 5 of the mandibular advancement device 1 can be selectively changed by a precise distance relative to the upper tray assembly 3 to meet the changing needs of the patient during sleep over time.

More particularly, a pair of position control push pads 56 are located at and integral to opposite sides of the lower chassis 10 of the lower tray assembly 5. A position indicator 58 is molded into or printed onto each of the push pads 56. The pair of position control push pads 56 are responsive to compressive squeezing forces (best illustrated in FIGS. 3 and 4) applied thereagainst by the patient in order to cause the shape of the lower chassis 10 to be momentarily deformed so that the rows of teeth 32 and 50 are temporarily disengaged. The patient can now apply a pushing force to slidably relocate and change the position of the lower tray assembly 5 relative to the upper tray assembly 3 to achieve a result that will soon be described.

A position indication scale 60 is located at and integral to each side of the upper chassis 9 of the upper tray assembly 3. A series of position lines are molded into or printed onto each of the scales 60. The increments between each successive pair of position lines of the scales 60 corresponds to a pre-determined linear distance (e.g., one millimeter). In the assembled configuration of the mandibular appliance 1 (best shown in FIGS. 2-5) after the lower tray assembly 5 has been moved into sliding mating engagement below the upper tray assembly 3, the position indication scale 60 at each side of the upper chassis 9 is located directly above the position control push pad 56 at each side of the lower chassis 10. The position indicator 58 of each push pad 56 points to a position line which corresponds to a particular distance along each position indication scale 60.

Figure 2:
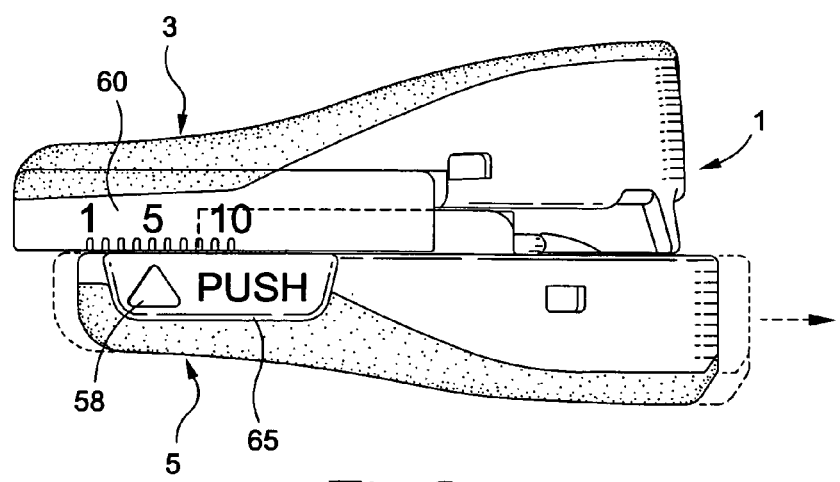
FIG. 2 shows the mandibular advancement device of FIG. 1 according to a preferred embodiment outside the mouth of the patient and after adjustment.

Thus, as the position of the lower tray assembly 5 is slidably adjusted below the upper chassis 9 in the manner shown in FIG. 2, the position indicators 58 of the position control pads 56 will be displaced an identical distance along the position indication scales 60 to provide the patient with a visual indication of the position of the lower tray assembly 5 with respect to the upper tray assembly 3. In this way, the patient can make regular controllable and precise position adjustments to the lower tray assembly 5 for an advantage that will be described when referring hereinafter to FIG. 1.

The mandibular advancement appliance 1 also includes a flexible tongue support wire 62 that can be bent and shaped as needed. The tongue support wire 62 is preferably manufactured from stainless steel, or the like, and is shown with a rearward bend 66 to establish a seat upon which a tongue rest 68 (of FIGS. 3, 4 and 6) is laid. The tongue rest 68 is pivotally connected to or molded over the top of the wire 62. The tongue rest 68 is ideally manufactured from a low durometer silicone or urethane and is suspended by the tongue support wire 62 so as to be positioned in the oral cavity and sit on top of the patient's tongue to thereby prevent the tongue from falling back in the mouth and blocking the patient's airway while the patient sleeps on his back with the appliance 1 in his mouth.

The opposite ends 70 of the tongue support wire 62 (best shown in FIG. 9) between which the rearward bend 66 is located are detachably connected to and releasably retained by respective ones of the pair of position adjustment blocks 48 at the lower chassis 10 of the lower tray assembly 5. At the same time, the tongue rest support wire 62 is positioned behind and engaged by a pair of wire stops 71 that stand upwardly from the lower chassis 10 to retain the wire 62 in place atop the lower tray assembly 5. When the tongue support wire 62 is detachably connected to the position adjustment blocks 48 and engaged by the wire stops 71, the lower chassis 10 is press fit into attachment with the lower bite impression tray 12 to complete the lower tray assembly 5 of the mandibular advancement appliance (of FIGS. 9 and 10). The rearward bend 66 in the tongue support wire 62 is thusly located within the oral cavity surrounded by the arcuate lower chassis 10 and the lower bite impression tray 12 at which the tongue rest 68 (of FIGS. 3 and 4) will engage the patient's tongue following the insertion of the appliance 1 into the patient's mouth. Because of comfort considerations during use, the patient may wish to separate the tongue support wire 62 from the lower tray assembly 5. In this case, the ends 70 of tongue support wire 62 are pulled out of their detachable connection with the position adjustment blocks 48 and the wire 62 is disengaged from the wire stops 71 so that the wire 62 and tongue rest 68 are removed together from the appliance 1.

Figure 9:
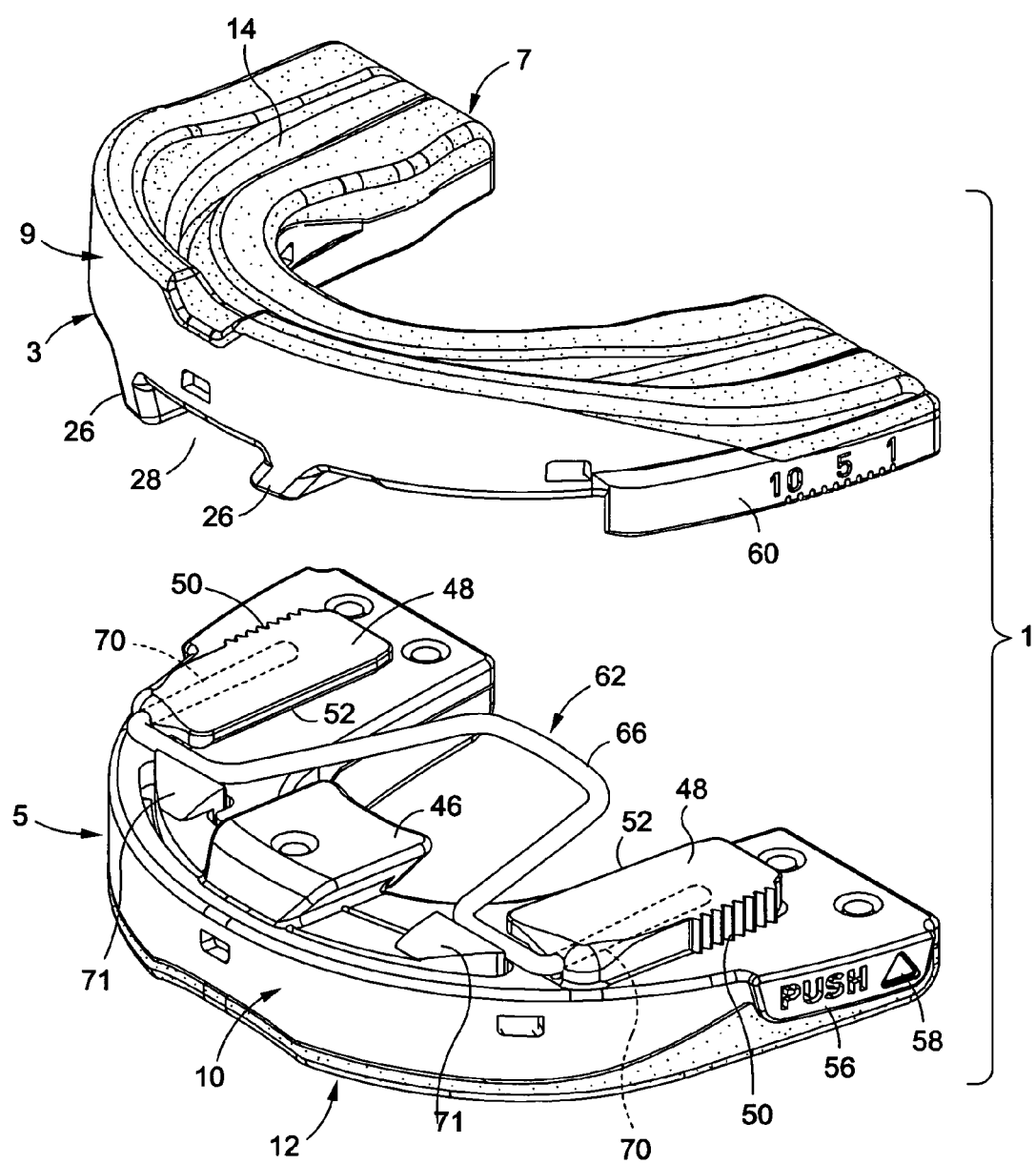
FIGS. 9 and 10 show top and bottom perspective views of upper and lower tray assemblies prior to their being mated together to complete the mandibular advancement device.
Figure 10:
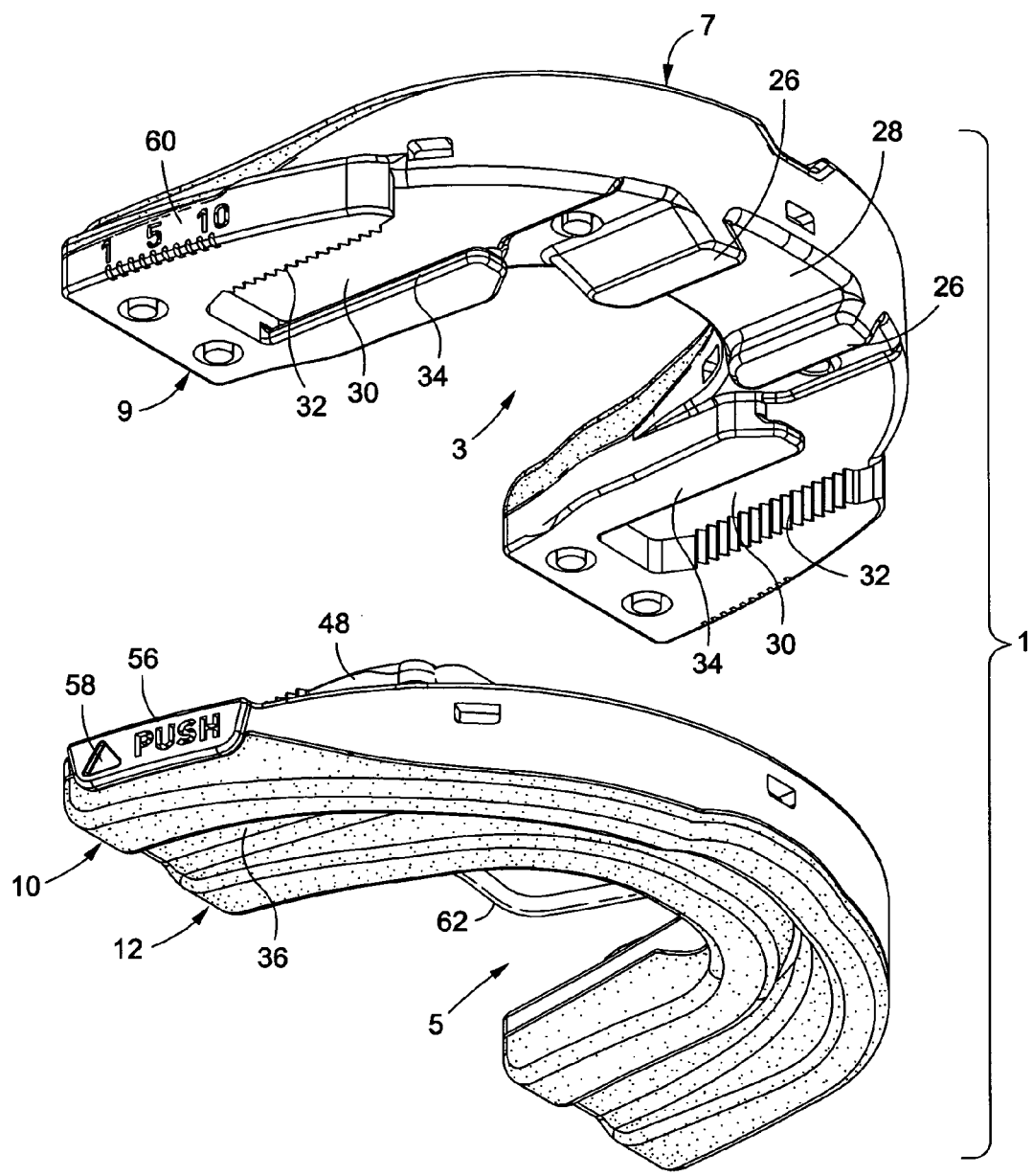

FIGS. 9 and 10 of the drawings show the upper tray assembly 3 positioned over the top of the lower tray assembly 5. The upper and lower tray assemblies 3 and 5 are mated to one another to complete the mandibular advancement device 1 when, as previously described, the centering guide 46 which stands upwardly from the lower chassis 10 of the lower tray assembly 5 slides through the guide path 28 between the guide walls 26 of the upper chassis 9 of the upper tray assembly 3 and the position adjustment blocks 48 from the lower chassis 10 of the lower tray assembly 5 are pushed into sliding interlocking engagement with the locking channels 30 at the upper chassis 9.

FIGS. 3-6 of the drawings show the intra-oral mandibular advancement appliance 1 in the assembled ready-to-use configuration after the upper tray assembly 3 and the lower tray assembly 5 have been moved into sliding interlocking engagement with one another in the manner just explained. The tongue support wire 62 is shown detachably connected to the position adjustment blocks 48 at the lower chassis 10 of the lower tray assembly 5. In this case, the tongue rest 68 which is attached to the rearward bend 66 of the tongue support wire 62 is shown suspended from wire 62 so as to be surrounded by the arcuate upper and lower tray assemblies 3 and 5 and positioned so as to sit upon the patient's tongue after the appliance 1 has been inserted within the patient's mouth. That is, and as was previously described, the tongue rest 68 prevents the patient's tongue from falling (under the influence of gravity) towards his throat during sleep so that the windpipe will not be blocked.

As an option, the tongue rest 68 is provided with a series of cutting grooves 72. A scissors or similar cutting tool may be used to cut the tongue rest 68 along one of the cutting grooves 72 so that the tongue rest can be shortened by a precise amount depending upon the size of the patient's tongue and comfort considerations.

Figure 3:
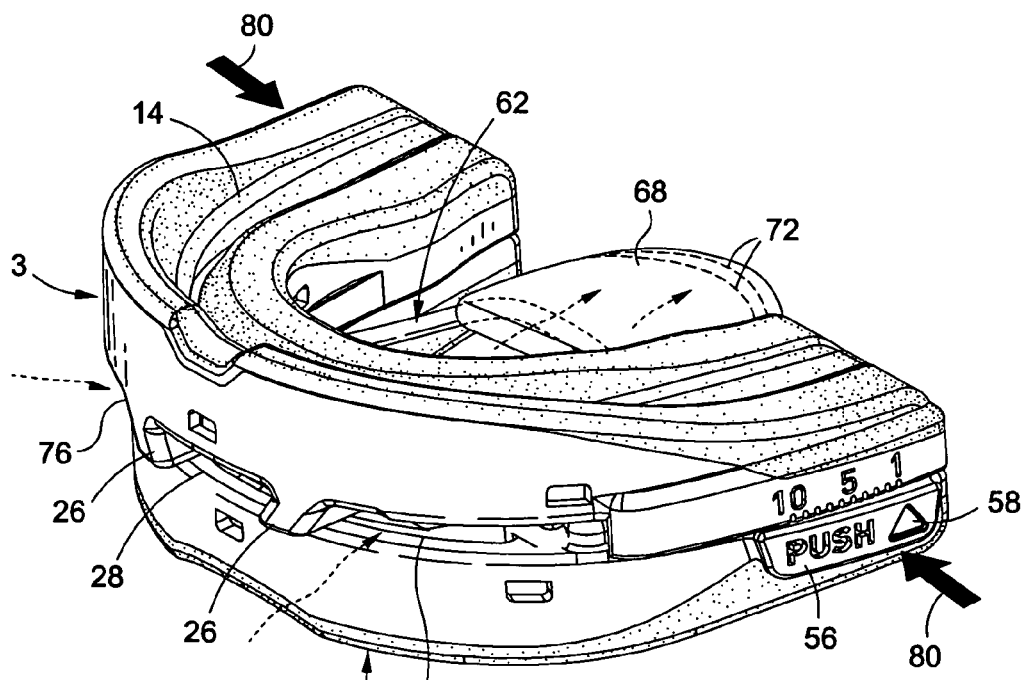
FIGS. 3 and 4 show front and rear perspective views of the mandibular advancement device prior to adjustment.

As is best shown in FIG. 3, with the upper tray assembly 3 lying above the lower tray assembly 5, a pair of air flow passages 76 are established through the mandibular advancement appliance 1. In particular, the guide retention walls 26 at the upper chassis 9 of the upper tray assembly 3 between which the guide path 28 is located create gaps between the upper and lower tray assemblies 3 and 5 for the air flow passages 76 through apparatus 1. The air flow passages 76 are especially helpful for patients with a deviated septum or a closed nostril to facilitate breathing by ensuring a continuous air flow while the apparatus is used during sleep.

Prior to using the mandibular advancement appliance 1 for the first time during sleep, the patient boils a pot of water within which the appliance is placed and heated. The heated appliance 1 is then removed from the boiling water by means of tongs or a similar tool and permitted to cool until it becomes warm. While still warm, the appliance 1 is inserted in the patient's mouth at which time the patient closes his mouth and bites on the relatively soft upper bite impression tray 7 and the lower bite impression tray 12. The patient's upper set of teeth bites down against the bite channel 14 of the upper bite impression tray 7, and his lower set of teeth bite up against the bite channel 36 of the lower bite impression tray 12. Impressions of the upper and lower sets of teeth are shaped in the opposing relatively soft bite channels 14 and 36 which, as previously explained, are compressed against the relatively hard upper and lower chassis 9 and 10.

At the same time that the patient bites on the upper and lower bite impression trays 14 and 36, the corresponding pressure generated by the upper and lower sets of teeth force the locking pins 16 (of FIG. 8) and 38 (of FIG. 7) to move completely through their respective oppositely-aligned locking pin holes 20 and 42, whereby the soft upper bite impression tray 7 is affixed to the hard upper chassis 9 to finalize the assembly of the upper tray assembly 3 and the soft lower bite impression tray 12 is affixed to the hard lower chassis 10 to finalize the assembly of the lower tray assembly 5. Lastly, the appliance 1 is placed into a pot of ice water so that the impression of the patient's upper and lower sets of teeth in the bite channels 14 and 36 will be made permanent.

The intra-oral mandibular advancement appliance 1 of this invention is now ready to be used by the patient while he sleeps. Referring in this regard to FIG. 1 of the drawings, the appliance 1 is shown inserted in the mouth of the patient. As previously explained, the appliance 1 is advantageously adapted to position and controllably reposition the patient's lower jaw forward of his upper jaw so that an airway will be continuously opened to the patient's throat so as to minimize the effects of snoring and/or sleep apnea.

Figure 4:
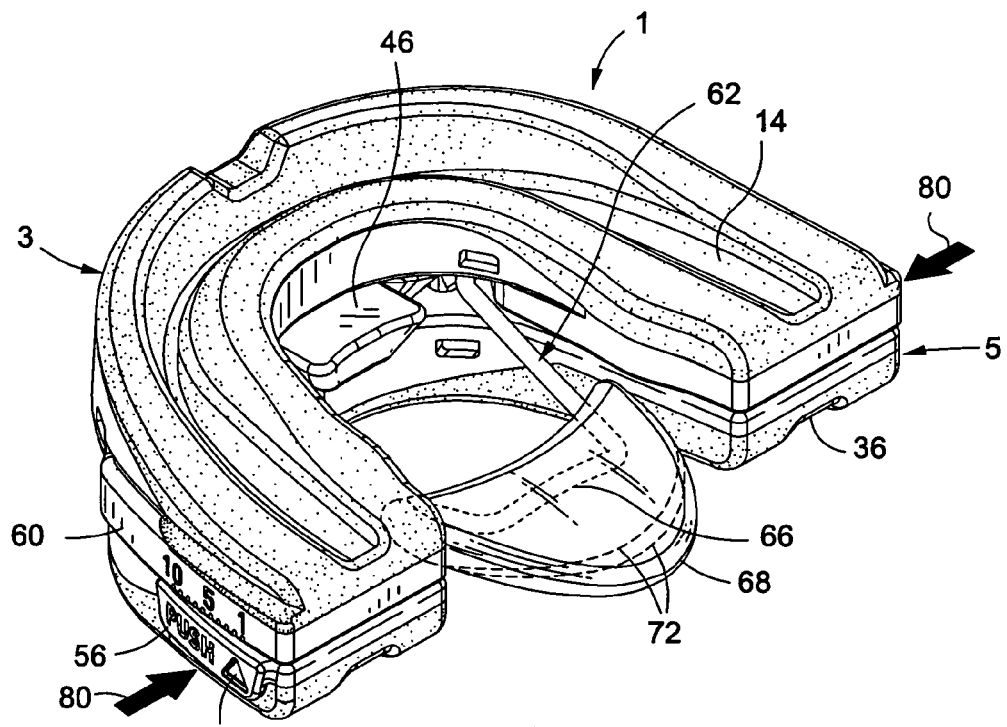
Figure 5:
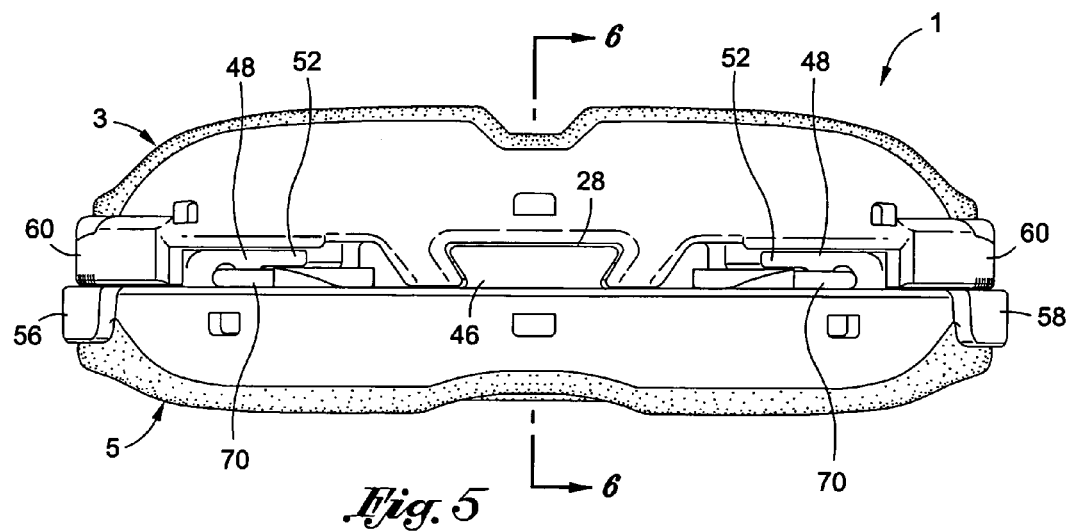
FIG. 5 shows a front view of the mandibular advancement device.
Figure 6:
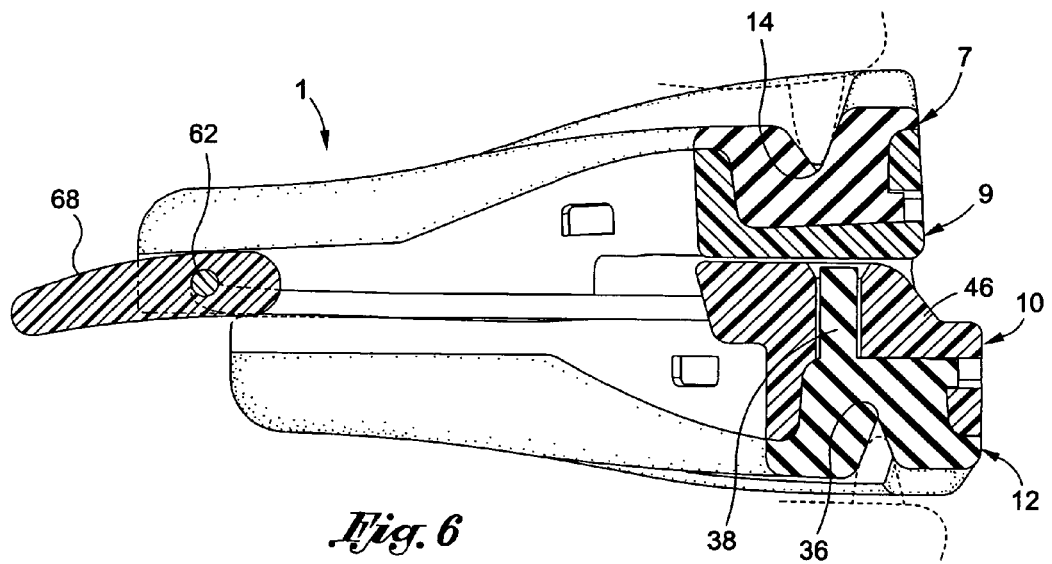
FIG. 6 is a cross-section of the mandibular advancement device taken along lines 6-6 of FIG. 5.

More particularly, the patient is provided with the ability to selectively adjust the mandibular advancement device 1 to prevent the occlusion of his windpipe by causing his lower jaw to be continuously moved forward to meet his changing needs over time. FIG. 2 illustrates the adjustable nature of the appliance 1 after the lower tray assembly 5 thereof is pushed from an initial position lying directly below the upper tray assembly 3 (as shown in FIGS. 3 and 4) to the adjusted position of FIG. 2 where the lower tray assembly 3 is advanced forward of the upper tray assembly 5. Inasmuch as the patient's upper and lower sets of teeth are received by the bite channels 14 and 36 of the upper and lower tray assemblies 3 and 5, the forward advancement of the lower tray assembly 5 relative to the upper tray assembly 3 will cause a corresponding forward displacement of the patient's lower jaw relative to his upper jaw.

At the same time that the lower tray assembly 5 moves relative to the upper tray assembly 3, the position indicator 58 molded into the position control push pad 56 of the lower tray assembly 5 will move a like distance below to the position indication scale 60 of the upper tray assembly 3 to provide the patient with a visual indication of the position of his lower jaw. That is to say, as the lower tray assembly 5 is slidably and forwardly advanced, the position indicator 58 carried thereby will move continuously along the position indication scale 60 in small (e.g., one millimeter) increments.

To accomplish the selective and continuous forward advancement of the lower tray assembly 5 of the mandibular advancement appliance 1 and the corresponding forward advancement of the patient's lower jaw, the patient applies compressive squeezing forces (designated by the directional arrows 80 in FIGS. 3 and 4) to the position control push pads 56 located at opposite sides of the lower chassis 10 of the lower tray assembly 5. The squeezing forces 80 momentarily deform the lower chassis 10 so that the teeth 50 along the position adjustment blocks 48 (of FIG. 9) of the lower chassis 10 are moved out of their meshing locking engagement with opposing teeth 32 along channels 30 (of FIG. 10) of the upper chassis 9. Accordingly, the patient can now pull the lower tray assembly 5 forward by any distance so that the position adjustment blocks 48 ride through respective ones of the locking channels 30.

When the forward position of the lower tray assembly 5 has been adjusted as necessary, the patient releases the squeezing forces applied to position control push pads 56 so that the original shape of the lower chassis 10 is restored. The mandibular advancement appliance 1 is then inserted in the patient's mouth as shown in FIG. 1 to be used during sleep. Should additional fine adjustments be required over time, such adjustments can be easily and accurately made by the patient at home in the manner described above and without the use of tools, springs, having to remove and return fasteners, or requiring the assistance of medical personnel.

The invention claimed is:

1. An intra-oral mandibular advancement appliance to be inserted in the mouth of a patient so as to permit the position of the lower jaw of the patient to be adjusted relative to the upper jaw to maintain an airway to the throat through which the patient can breathe while sleeping, said appliance comprising:

an upper tray assembly having an arcuate shape against which the teeth of the patient's upper jaw are seated, said upper tray assembly having a front and a pair of sides lying opposite and spaced from one another;

a lower tray assembly having an arcuate shape against which the teeth of the patient's lower jaw are seated, said lower tray assembly also having a front and a pair of sides lying opposite and spaced from one another;

a position adjustment block located at each of the pair of sides of one of said upper tray assembly and said lower tray assembly; and a locking channel located at each of the pair of sides of the other one of said upper tray assembly and said lower tray assembly, each position adjustment block being slidably received within a respective locking channel, whereby said lower tray assembly is mated in releasable locking engagement to said upper tray assembly to prevent a displacement of said lower tray assembly relative to said upper tray assembly, said lower tray assembly being responsive to a lateral compressive squeezing force simultaneously applied to the opposite sides thereof to temporarily change the shape of and deform said lower tray assembly to enable each position adjustment block to slide through its respective locking channel so as to release the locking engagement of said lower tray assembly to said upper tray assembly and thereby permit the positions of said lower tray assembly and the patient's lower jaw to be adjusted relative to the positions of said upper tray assembly and the patient's upper jaw.

2. The intra-oral mandibular advancement appliance recited in claim 1, wherein said lower tray assembly has a push pad located at each of said pair of sides for receipt of said lateral compressive squeezing force thereagainst so that the shape of said arcuate lower tray assembly can be temporarily changed and the position of said lower tray assembly adjusted relative to the position of said upper tray assembly.

3. The intra-oral mandibular advancement appliance recited in claim 2, wherein said push pad located at one side of said arcuate lower tray assembly has a position indicator and said upper tray assembly has a position indication scale, said position indicator moving along said position indication scale when the position of said lower tray assembly is adjusted relative to the position of said upper tray assembly.

4. The intra-oral mandibular advancement appliance recited in claim 1, further comprising a tongue rest held between the pairs of sides of said arcuate upper and lower tray assemblies and adapted to lay upon the tongue of the patient to prevent the tongue from falling across and blocking the patient's airway.

5. The intra-oral mandibular advancement appliance recited in claim 4, further comprising a tongue rest support to which said tongue rest is connected, said tongue rest support being detachably connected to the position control adjustment blocks located at the pair of sides of the one of said upper tray assembly and said lower tray assembly so that said tongue rest support and said tongue rest connected to said tongue rest support are detachable from said position control adjustment blocks.

6. The intra-oral mandibular advancement appliance recited in claim 1, wherein the position adjustment blocks and the locking channels located at the pair of sides of said arcuate upper and lower tray assemblies have respective sets of teeth running therealong, the sets of teeth of the position adjustment blocks meshing with the sets of teeth of said locking channels, whereby said lower tray assembly is mated in said releasable locking engagement to said upper tray assembly to prevent a displacement of said lower tray assembly relative to said upper tray assembly.

7. The intra-oral mandibular advancement appliance recited in claim 1, wherein each position adjustment block at each of the pair of sides of the one of said arcuate upper tray assembly and said arcuate lower tray assembly has a lip projecting therefrom, the lips projecting from said position adjustment blocks sliding along and being engaged by the pair of sides of the other one of said arcuate upper tray assembly and said arcuate lower tray assembly when said position adjustment blocks of said arcuate lower tray assembly slide through respective locking channels of said arcuate upper tray assembly.

8. The intra-oral mandibular advancement appliance recited in claim 1, wherein there is a centering guide located at and standing upwardly from the front of said arcuate lower tray assembly and a guide path located between a pair of guide path walls at the front of said arcuate upper tray assembly, said centering guide riding through said guide path between said guide path walls when the position adjustment blocks at the pair of sides of the one of said arcuate upper tray assembly and said lower tray assembly slide through the respective locking channels at the pair of sides of the other one of said arcuate upper tray assembly and said lower tray assembly.

9. The intra-oral mandibular advancement appliance recited in claim 1, wherein said upper tray assembly includes a relatively soft and impressionable upper bite portion against which the teeth of the patient's upper jaw are seated and a relatively hard and rigid upper chassis when compared to said upper bite portion, said upper bite portion lying over said upper chassis.

10. The intra-oral mandibular advancement appliance recited in claim 9, wherein the relatively soft and impressionable upper bite portion of said upper tray assembly has a bite channel formed therein within which the teeth of the patient's upper jaw are received, said upper bite portion being responsive to heat applied thereto such that an impression of the teeth of the patient's upper jaw is formed in said bite channel when the patient bites into said upper tray assembly and thereby compresses said relatively soft and impressionable upper bite portion against said relatively hard and rigid upper chassis.

11. The intra-oral mandibular advancement appliance recited in claim 10, wherein said lower tray assembly includes a relatively soft and impressionable lower bite portion against which the teeth of the patient's lower jaw are seated and a relatively hard and rigid lower chassis when compared to said lower bite portion, said lower bite portion lying over said lower chassis.

12. The intra-oral mandibular advancement appliance recited in claim 11, wherein the relatively soft and impressionable lower bite portion of said lower tray assembly has a bite channel formed therein within which the teeth of the patient's lower jaw are received, said lower bite portion being responsive to heat applied thereto such that an impression of the teeth of the patient's lower jaw is formed in said bite channel when the patient bites into said lower tray assembly and thereby compresses said relatively soft and impressionable lower bite portion against said relatively hard and rigid lower chassis.

13. An intra-oral mandibular advancement appliance to be inserted in the mouth of a patient so as to permit the position of the lower jaw of the patient to be adjusted relative to the upper jaw to maintain an airway to the throat through which the patient can breathe while sleeping, said appliance comprising:
  an upper tray assembly having an arcuate shape against which the teeth of the patient's upper jaw are seated, said upper tray assembly including a pair of sides lying opposite and spaced from one another;
  a lower tray assembly having an arcuate shape against which the teeth of the patient's lower jaw are seated, said lower tray assembly including a pair of sides lying opposite and spaced from one another and an upstanding position adjustment block located at each of said pair of sides and disposed in releasable locking engagement with said upper tray assembly, whereby to mate said upper and lower tray assemblies together and prevent a displacement of said lower tray assembly relative to said upper tray assembly; and
  a tongue rest projecting from said lower tray assembly and located between the pairs of sides of said upper and lower tray assemblies to lay upon the tongue of the patient and prevent the tongue from falling across and blocking the patient's airway, said tongue rest being detachably connected to the upstanding position adjustment blocks at the opposite sides of said lower tray assembly,
  said lower tray assembly being responsive to a lateral compressive squeezing force simultaneously applied to the opposite sides thereof to temporarily change the shape of and deform said lower tray assembly so as to release the locking engagement of said upstanding position adjustment blocks to said upper tray assembly and thereby permit the positions of said lower tray assembly and the patient's lower jaw to be adjusted relative to the positions of said upper tray assembly and the patient's upper jaw.

14. The intro-oral mandibular advancement appliance recited in claim 13, wherein said upper tray assembly has first and second channels recessed therein for the slidable receipt of the upstanding position adjustment blocks located at the opposite sides of said lower tray assembly, said position adjustment blocks and said first and second recessed channels having respective complementary sets of teeth that are meshed together, whereby said position adjustment blocks are disposed in said releasable locking engagement with said upper tray assembly and said upper and lower tray assemblies are mated together.

15. An intra-oral mandibular advancement appliance to be inserted in the mouth of a patient so as to permit the position of the lower jaw of the patient to be adjusted relative to the upper jaw to maintain an airway to the throat through which the patient can breathe while sleeping, said appliance comprising:
  an upper tray assembly against which the teeth of the patient's upper jaw are seated; and
  a lower tray assembly against which the teeth of the patient's lower jaw are seated,
  one of said upper tray assembly and said lower tray assembly including at least one upstanding position control block having at least one first set of teeth running therealong and the other one of said upper and lower tray assemblies having a locking channel recessed therein and having a complementary set of locking teeth running therealong, said position adjustment block being received within said recessed locking channel such that said first and complementary sets of teeth are meshed together in releasable interlocking engagement to prevent a displacement of said lower tray assembly relative to said upper tray assembly,
  said lower tray assembly being responsive to a lateral compressive squeezing force applied thereto to correspondingly change the shape of and deform said lower tray assembly and thereby enable the first and complementary sets of teeth of said position adjustment block and said locking channel to be released from their interlocking engagement with one another so as to permit said upstanding position adjustment block to slide through said recessed locking channel whereby the positions of said lower tray assembly and the patient's lower jaw are correspondingly adjusted relative to the positions of said upper tray assembly and the patient's upper jaw.

16. The intro-oral mandibular advancement appliance recited in claim 15, wherein there is a centering guide standing upwardly from one of said upper and lower tray assemblies and a guide path formed between a pair of guide path walls located at the other one of said upper and lower tray assemblies, said upstanding centering guide riding through said guide path between said guide path walls at the same time that said position adjustment block slides through the said locking channel and the positions of said lower tray assembly and the patient's lower jaw are adjusted.

17. The intro-oral mandibular advancement appliance recited in claim 15, wherein said at least one upstanding position control block has a lip projecting therefrom and said at least onen recessed locking channel has a catch lying thereabove, said lip sliding below and being captured by said catch, whereby said position control block is retained within said channel and said upper and lower tray assemblies are mated together.

18. The intra-oral mandibular advancement appliance recited in claim 15, wherein each of said upper and lower tray assemblies has an arcuate shape with a front and a pair of sides that are spaced from and located opposite one another, the one of said arcuate upper and lower tray assemblies having said at least one upstanding position control block located at each of said pair of sides thereof, and the other one of said arcuate upper and lower tray assemblies having said at least one locking channel recessed within each of said pair of sides for the slidable receipt of respective ones of said position control blocks, said lower tray assembly being responsive to said lateral compressive squeezing force simultaneously applied to the pair of sides thereof.

19. The intra-oral mandibular advancement appliance recited in claim 18, further comprising a tongue rest held between the pair of sides of each of said arcuate upper and lower tray assemblies and adapted to lay upon the tongue of the patient to prevent the tongue from falling across and blocking the patient's airway, and a tongue rest support to which said tongue rest is connected, said tongue rest support being detachably connected to the upstanding position control blocks located at the pair of sides of the one of said upper and lower tray assemblies.

20. The intra-oral mandibular advancement appliance recited in claim 15, wherein each of said upper and lower tray assemblies has a relatively soft and impressionable bite portion against which respective sets of the teeth of the patient's upper and lower jaw are seated and a relatively hard and rigid chassis when compared to said bite portion, said bite portion lying over said chassis.

* * * * *